US00PP13781P29

(12) United States Plant Patent
Hofmann

(10) Patent No.: US PP13,781 P2
(45) Date of Patent: May 6, 2003

(54) VARIETY OF GERANIUM PLANT NAMED 'FIWOCHERRY'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/120,172

(22) Filed: Apr. 10, 2002

(51) Int. Cl.[7] ..... A01N 5/00
(52) U.S. Cl. ..... Plt./330
(58) Field of Search ..... Plt./330

*Primary Examiner*—Kent Bell
(74) *Attorney, Agent, or Firm*—Webb Ziesenhiem Logsdon Orkin & Hanson, P.C.

(57) ABSTRACT

A new and distinct zonal geranium plant named 'Fiwocherry', having cherry colored flowers and reniform shaped leaves exhibiting compact growth.

1 Drawing Sheet

VARIETAL DENOMINATION

'Fiwocherry'.

BOTANICAL CLASSIFICATION

*Pelargonium×hortorum (zonal geranium).*

BACKGROUND OF THE INVENTION

The present invention comprises a new and distinct cultivar of *Pelargonium×hortorum* known by the varietal name 'Fiwocherry'. The new variety was discovered in a selective breeding program in Dresden, Germany. The new variety is the result of a combination breeding of unnamed, unpatented selections from breeding group 8K-20. The new variety exhibits the growth and branching of its heritage, but differs in its flower color. The new variety was first asexually reproduced by cuttings in Dresden, Germany in 1999. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. Plants described were about 9 months old. The color readings were taken indoors on plants grown in pots in greenhouses during summer. Color references are primarily to The R.H.S. Colour Chart of The Royal Horticultural Society of London.

PLANT

Form: Upright.
Height from media surface to top of foliage: 25–30 cm.
Height from media surface to top of umbels: 35–40 cm.
Growth: Erect, well branched.
Strength: Does not require artificial support.
Roots: Adventive, 3.5 weeks to develop, 155D.

Time to produce a flowering plant: 3 months.
Leaves: Opposite arrangement, zone present.
*Length.*—4 cm.
*Width.*—7.5 cm.
*Shape.*—Overall: Reniform. Base: Cordate. Apex: Pointed.
*Margin.*—Entire with deeply incised lobes.
*Texture.*—Hairy.
*Color.*—Upper surface: 137A with zone of 147A. Lower surface: 137C.
Ribs and veins:
*Venation.*—Net-veined.
*Color.*—137D.
Petioles:
*Color.*—137D.
*Length.*—5 cm.
Stem/branches:
*Color.*—137D.
*Overall stem length.*—22–27 cm.
*Internode length.*—2.0–3.0 cm.
*Lateral branch length.*—22 cm.

THE BUD

When just beginning to open:
Shape:
*Overall.*—Umbel-shaped.
*Individual bud.*—Spindle-shaped.
Color: 43A.
Size when just showing color:
*Cluster.*—4 cm in diameter.
*Individual bud.*—Length: 1.2 cm. Width: 0.5 cm.

INFLORESCENCE

Flowering: Continuous through summer until frost.
Borne: Umbel; flower on pedicel, pedicel on peduncle.
Umbel:
*Width.*—8 cm.
*Depth.*—4 cm.
*Number of flowers per umbel.*—About 40.
*Lastingness.*—3–5 weeks.
Flowers:
*Form.*—Zygomorph, single.
*Size.*—Diameter: 3.5–4.0 cm. Depth: 1.0 cm.

*Petals.*—Color: Upper surface: 52A. Lower surface: 46D. Quantity: 5 per flower. Size: Length: Upper petal: 2.2 cm. Lower petal: 2.0 cm. Width: Upper petal: 0.7 cm. Lower petal: 1.4 cm. Shape: Overall: Upper petal: Narrow/pointed. Lower petal: Oval. Apex: Pointed. Base: Pointed. Margin: Serrated. Texture: Smooth.

Petaloids: Absent.

Sepals:

*Shape.*—Overall: Narrow, linear. Apex: Pointed. Base: Fused.

*Color.*—Upper Surface: 143A. Lower Surface: 143A.

*Size.*—Length: 0.8 cm. Width: 0.2 cm.

Pedicel:

*Length.*—2.5–3.0 cm.

*Color.*—184B.

Peduncle:

*Length.*—16 cm.

*Color.*—139C.

Disease/pest resistance: No susceptibility to diseases or pests noted to date.

REPRODUCTIVE ORGANS

Stamens:

*Anthers.*—3 mm long.

*Filaments.*—Length: 4 mm. Color: 52B.

*Pollen.*—25A.

Pistils:

*Number.*—One, five parted.

*Length.*—2 mm.

*Stigma.*—53B.

*Style.*—Length: 0.6 cm. Color: 53D.

Ovaries: Superior, hairy.

*Length.*—0.4 cm.

*Color.*—138 C.

Fruit: If present, maximum 5 per flower, 0.3–0.4 cm long, 165A.

GENERAL CHARACTERISTICS

1. Cherry red flower color.
2. Reniform shaped leaves.
3. Compact growth.
4. Single flowering.
5. Green zonation.
6. Tetraploid.
7. Heat tolerant.

I claim:

1. A new and distinct variety of geranium plant substantially as shown and described.

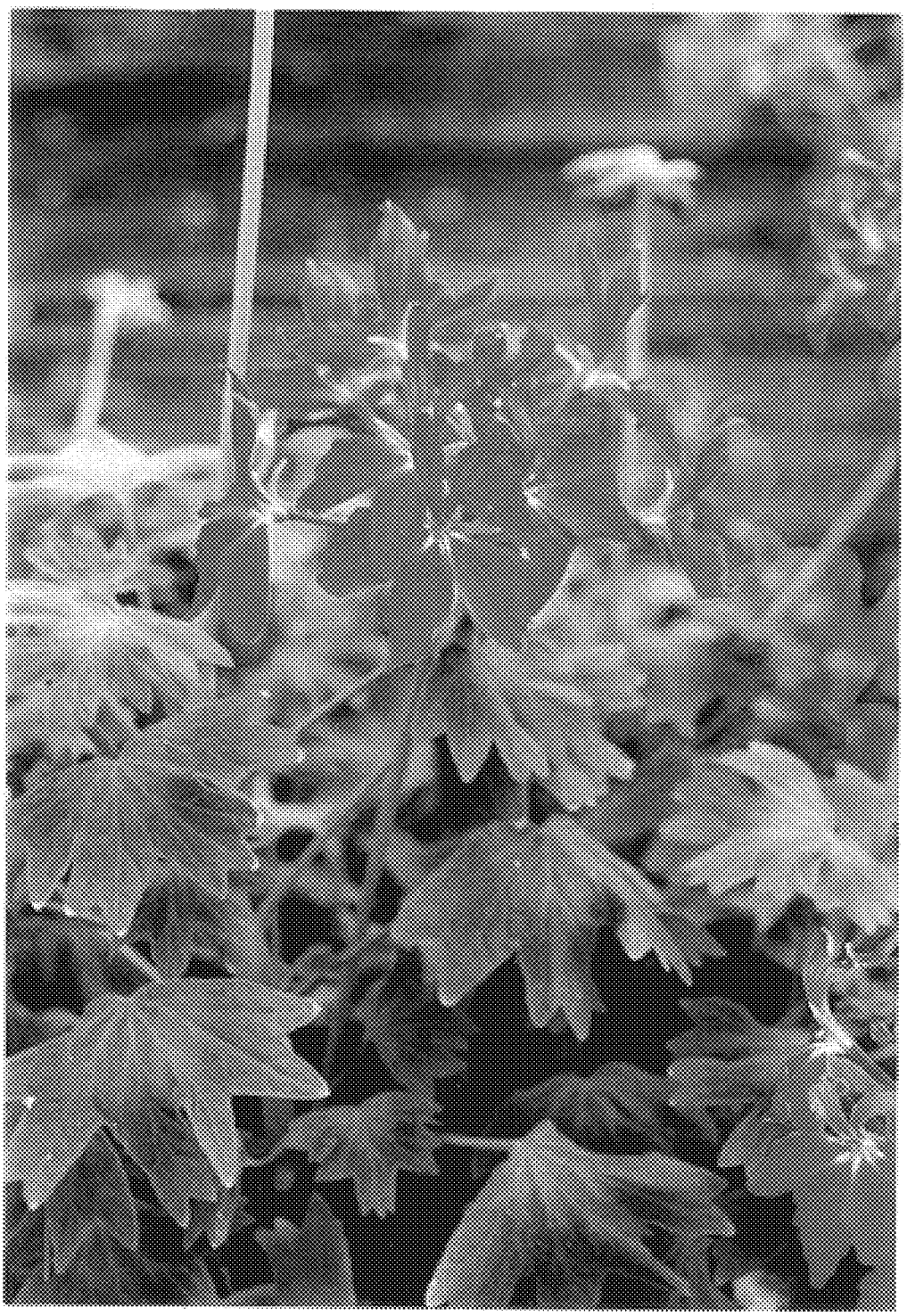

* * * * *